United States Patent
Xu et al.

(10) Patent No.: US 9,878,093 B2
(45) Date of Patent: Jan. 30, 2018

(54) MINIATURE PORTABLE MULTIFUNCTIONAL INFUSION DEVICE

(71) Applicant: THE FOURTH MILITARY MEDICAL UNIVERSITY, Xi'an, Shaanxi (CN)

(72) Inventors: Lixian Xu, Shaanxi (CN); Shengwu Zhang, Shaanxi (CN)

(73) Assignee: THE FOURTH MILITARY MEDICAL UNIVERSITY, Xi'an, Shaanxi (CN)

( * ) Notice: Subject to any disclaimer, the term of this patent is extended or adjusted under 35 U.S.C. 154(b) by 349 days.

(21) Appl. No.: 14/890,878

(22) PCT Filed: Jun. 17, 2013

(86) PCT No.: PCT/CN2013/077310
§ 371 (c)(1),
(2) Date: Nov. 12, 2015

(87) PCT Pub. No.: WO2014/166157
PCT Pub. Date: Oct. 16, 2014

(65) Prior Publication Data
US 2016/0074578 A1    Mar. 17, 2016

(30) Foreign Application Priority Data
Apr. 10, 2013  (CN) .......................... 2013 1 0123794

(51) Int. Cl.
*A61M 5/145* (2006.01)
*A61M 5/142* (2006.01)
*A61M 5/44* (2006.01)

(52) U.S. Cl.
CPC .... *A61M 5/14586* (2013.01); *A61M 5/14244* (2013.01); *A61M 5/44* (2013.01); *A61M 2005/14272* (2013.01)

(58) Field of Classification Search
CPC .. A61M 5/1413; A61M 5/14; A61M 5/14586; A61M 5/14248; A61M 5/14244;
(Continued)

(56) References Cited

U.S. PATENT DOCUMENTS

2007/0106218 A1*  5/2007  Yodfat ................ A61M 5/1413
604/131

* cited by examiner

*Primary Examiner* — Andrew Gilbert
*Assistant Examiner* — Hamza Darb

(57) ABSTRACT

A miniature portable multifunctional infusion device includes a liquid bottle (4) and a film box body (16) secured to a support frame (1). The film box body (16) is respectively provided with a directional input interface (17) and a directional output interface (14) in communication with the liquid bottle (4) and a needle via an infusion pipe. The film box body (16) is installed with an elastic film (27), and a transmission system (31) is arranged at a side of the elastic film (27). The transmission system (31) includes a miniature direct current motor (32) connected to a frequency modulating system (28). The miniature direct current motor (32) is connected to a spiral straightening device (34) via a speed reducer (33), and the spiral straightening device (34) is connected to a reciprocating film propping device (36) via a two-order shaft (43). A truncated cone (39) of the reciprocating film propping device (36) at a front end is in contact with the elastic film (27). In the infusion device, the miniature direct current motor (32) drives the transmission system (31) to enable movement of the reciprocating film propping device (36), thereby realizing conversion from electrical energy to mechanical energy, and realizing regulation of an infusion speed through a change in the volume the reciprocating film propping device (36) by compressing the film box body (16).

10 Claims, 3 Drawing Sheets

(58) Field of Classification Search
CPC .......... A61M 5/16804; A61M 5/16831; A61M 5/16877; A61M 5/16886; A61M 5/14216
See application file for complete search history.

MINIATURE PORTABLE MULTIFUNCTIONAL INFUSION DEVICE

CROSS REFERENCE OF RELATED APPLICATION

This is a U.S. National Stage under 35 U.S.C. 371 of the International Application PCT/CN2013/077310, filed Jun. 17, 2013, which claims priority under 35 U.S.C. 119(a-d) to CN201310123794.6, filed Apr. 10, 2013.

FIELD OF THE TECHNOLOGY

The present invention relates to the field of medical instruments and, in particular, to a miniature portable multifunctional infusion device.

BACKGROUND

Currently, intravenous infusion is the most common and widespread clinical method in clinical treatment of foreign and domestic medical institutions, according to investigation, 90% of patients are subject to treatment of intravenous injection. Almost 100% of inpatients for surgery need to take the intravenous injection, and according to statistics of related departments, for 1.3 billion people in China, each person is subject to up to 8 dropping bottles annually on average, and infusion quantity reaches up high to 10.4 billion bottles. Nowadays, with improvement in science and technology as well as rapid development in medical field, a conventional infusion method still uses a fixed hanger invented by "Murphy" more than one hundred years ago, i.e. hang over a dropping bottle (pack) at a position higher than a puncture site of a patient to a certain height.

This conventional infusion method needs assistance from a fixed hanger mainly due to the limitations of infusion dynamics, which has many defects during practical use: 1) a patient is in a relatively fixed posture, and activities thereof are restricted apparently, it may be seen in medical institutions that a patient lifts an infusion bottle by oneself or lifts an infusion bottle escorted by the family to walk up and down stairs for various examinations, even goes to the bathroom; 2) it is difficult to transport the wounded, outside the hospital, there is no sufficient space to rotate a dropping bottle during battlefield and field rescue as well as patient transportation (using ambulance), the dropping bottle swings too much during driving, which is neither safe nor efficient for infusion, to transport the wounded at the battlefront, position thereof may be given away easily when the infusion rack and liquid sway, which is of poor concealment; and 3) infusion speed cannot be controlled accurately, during a process of saving high risk patients who are subject to severe loss of blood and dehydration, accurately injecting certain amount of liquid within a specified time cannot be implemented.

In addition to the conventional method above, an automatic pneumatic-type infusion device, an automatic pump-type infusion device, and a microcontroller-based portable medical automatic infusion device occur in recent years.

For the automatic pneumatic-type infusion device, a gas delivering pipeline is connected to a gas delivering pump at one end, and air is injected into the liquid bottle by the pump via an air filter to increase pressure within the liquid bottle, so that an objective of automatic infusion is achieved. Its defects lie in that, an infusion rack is also needed to hang the liquid bottle and an extra power source and gas delivering pump are needed, which generally does not have obvious advantages compared to the conventional method;

For the automatic pump-type infusion device and the microcontroller-based portable medical automatic infusion device, their main structure is a unique piping system formed of a dropping pack, a pump chamber, a pipeline and an injection needle. An integrated circuit controls a pushing lever to press the pump chamber, and automatic infusion is achieved by pipeline external control, various liquid medicines may be injected into veins in a specified amount at regular time. Hanging is avoided during infusion, the patient may move freely, however, the defects lie in that, the infusion pump has a large volume and needs to be driven by a power source, which requires high techniques and is difficult to be used widely in medical institutions at different levels.

An automatic inflatable pack-type infusion device includes an air bag, two independent chambers, a liquid filling pipe and an inflatable pipe, where the two chambers are separated by a flexible spacer layer, the inflatable pipe is in communication with one chamber, and the liquid filling pipe is in communication with the other chamber, and gas is pressed into space between an inner pack and an outer pack of an infusion pack with hands by utilizing one gasbag, so that pressure is generated from liquid within the inner pack, and the liquid is injected into patient body in a controllable the flow rate by pressure. The device is easy for use and convenient for carry (which may be hung around waist), and defects such as blood return will not occur. Principles of the automatic inflatable pack-style infusion device are fundamentally the same with principles of pressurized blood transfusion commonly used in clinical, of which a defect lies in a need for a continuous manual inflation, otherwise the liquid cannot overcome resistance from the blood to enter into blood vessels, thus burden for conventional infusion management is increased and the device is difficult to be promoted and used in the clinic treatment.

SUMMARY

An objective of the present invention is to provide a miniature portable multifunctional infusion device, which changes traditional infusion dynamics and does not need to secure a liquid bottle to a position above a patient, thereby being capable of placing a dropping bottle at any position for infusion and capable of accurately regulating infusion speed.

In order to achieve the above objective, the present invention uses the following technical solutions: including a support frame and a liquid bottle and a film box body secured thereto, where the film box body is respectively provided with a directional input interface and a directional output interface in communication with the liquid bottle and a needle via an infusion pipe, the film box body is installed with an elastic film, and a transmission system is arranged at a side of the elastic film, where the transmission system includes a miniature direct current motor connected to a frequency modulating system, the miniature direct current motor is connected to a spiral straightening device via a speed reducer, and the spiral straightening device is connected to a reciprocating film propping device via a two-order shaft, a truncated cone of the reciprocating film propping device at a front end is in contact with the elastic film, the frequency modulating system includes a miniature direct current power source connected to the miniature direct current motor, the miniature direct current power source is further connected to a controller for controlling the miniature direct current motor via a potentiometeric sensor, and the controller is further connected with a controller parameter input keyboard.

The reciprocating film propping device includes a flat body, a course adjusting mechanism mounted in a sliding sleeve, a trapezoidal transition section and the truncated cone which are arranged from back to front sequentially, and the trapezoidal transition section is mounted with a plate-type spring.

An outer side of the flat body is further installed with a distance sensor in connection with the controller.

A rear end of the flat body is further installed with a speed rotatable handle for adjusting flow rate of liquid within the film box body, a speed selecting pointer installed on the speed rotatable handle, and an infusion speed dial corresponding to the speed selecting pointer.

The film box body is further installed with a flow rate display.

The infusion pipe between the film box body and the needle is further provided with a liquid medicine heating control system, and the liquid medicine heating control system includes a pagoda-type heater enwinding the infusion pipe in contact with a heating power source, the pagoda-type heater is installed with a temperature sensor at an end, the pagoda-type heater and the temperature sensor are connected to a temperature controller respectively, and an infusion pipe at a front end of the needle is provided with a liquid medicine precision filter.

The support frame includes a bottle holder installed with the liquid bottle and a crescent holder installed with the film box body, the bottle holder is provided with a binder, a head restraint and an adjusting foundation which fasten the liquid bottle, and the crescent holder is provided with an absorber, and the support frame is further opened with a fitted aperture.

The film box body is further provided with a fast-assembling head restraint.

The directional output interface is further provided with a gas identifier.

The controller is installed with an acousto-optical warning display and a transmitter in connection with a weight sensor of the liquid bottle.

According to the present invention, the miniature direct current motor drives the transmission system to enable movement of the reciprocating film propping device, thereby realizing conversion from electrical energy to mechanical energy, realizing liquid injection by means of compressing the film box body by the reciprocating film propping device, and realizing accurate regulation of an infusion speed through controlling a volume at which the truncated cone is in contact with the elastic film.

Figure 1:
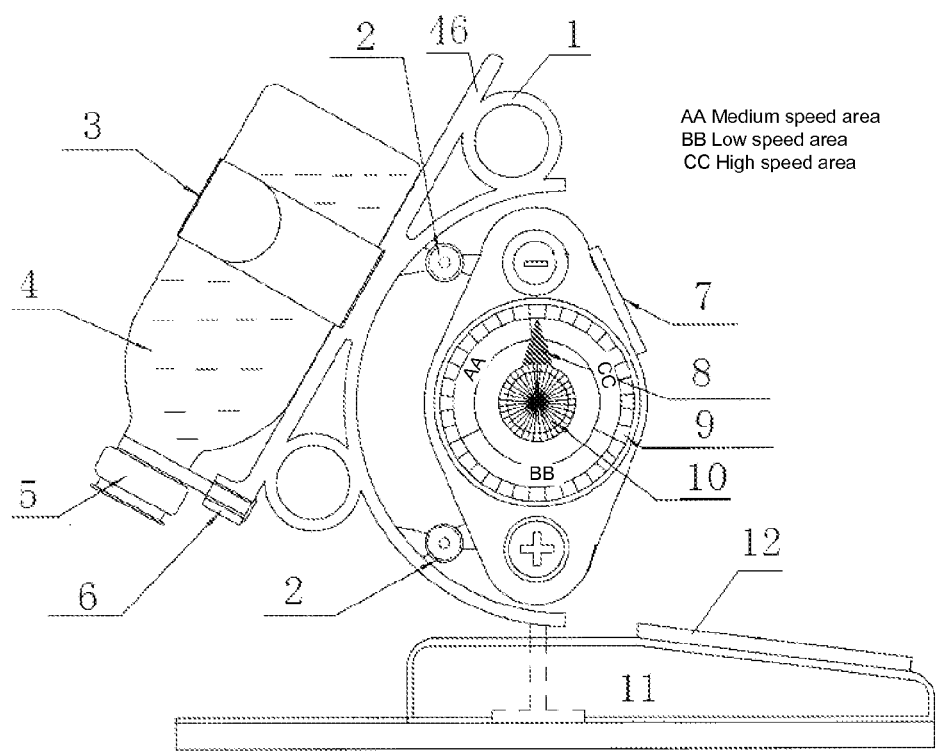
FIG. 1 is a front view of a miniature portable multifunctional infusion device according to the present invention.
Figure 2:
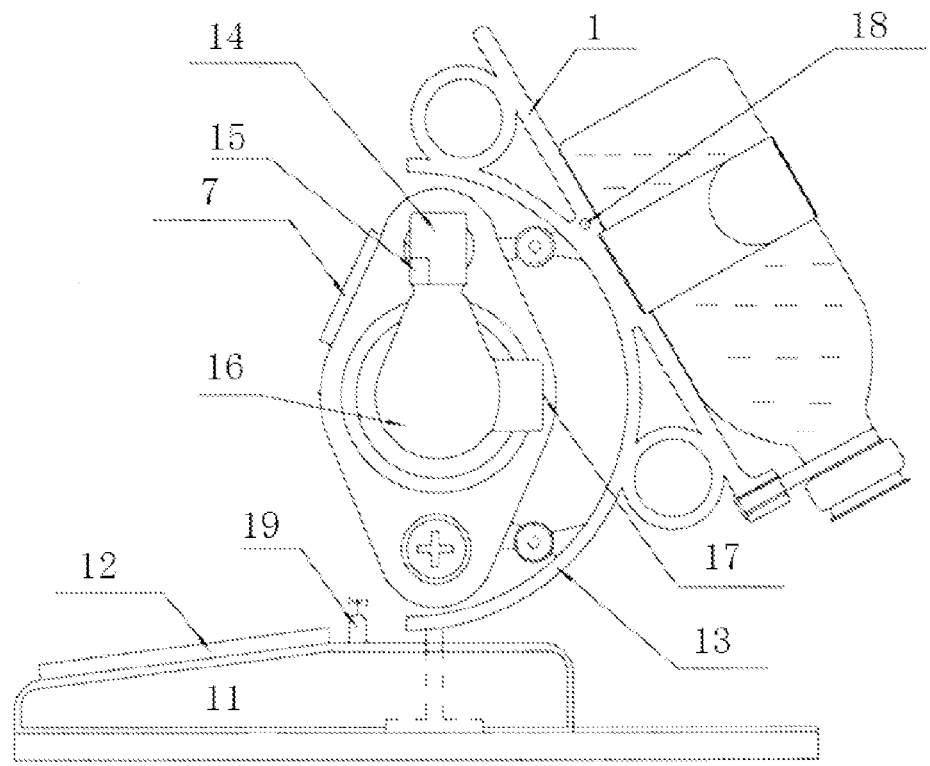
FIG. 2 is a back view of a miniature portable multifunctional infusion device according to the present invention.

In which, 1. support frame; 2. absorber; 3. binder; 4. liquid bottle; 5. head restraint; 6. adjusting foundation; 7. flow rate display; 8. speed selecting pointer; 9. infusion speed dial; 10. speed rotatable handle; 11. controller; 12. controller parameters input keyboard; 13. crescent holder; 14. directional output interface; 15. gas identifier; 16. film box body; 17. directional input interface; 18. fitted aperture; 19. transmitter; 20. needle; 21. liquid medicine precision filter; 22. liquid medicine heating control system; 23. temperature controller; 24. heating power source; 25. pagoda-type heater; 26. temperature sensor; 27. elastic film; 28. frequency modulating system; 29. potentiometeric sensor; 30. miniature motor power source; 31. transmission system; 32. miniature direct current motor; 33. speed reducer; 34. spiral straightening device; 35. distance sensor; 36. reciprocating film propping device; 37. flat body; 38. trapezoidal fine lines; 39. truncated cone; 40. course adjusting mechanism; 41. fast-assembling head restraint; 42. acousto-optical warning display; 43. two-order shaft; 44. plate-type spring; 45. sliding sleeve; and 46. bottle holder.

DETAILED DESCRIPTION

The present invention is further described in detail with reference to accompanying drawings hereunder.

Referring to FIG. 1-FIG. 4, the present invention includes a support frame 1 and an liquid bottle 4 secured thereto and a film box body 16 installed with a flow rate display 7, where the support frame 1 includes a bottle holder 46 installed with the liquid bottle 4 and a crescent holder 13 installed with the film box body 16, the bottle holder 46 is provided with a binder 3, a head restraint 5 and an adjusting foundation 6 which fasten the liquid bottle 4, the crescent holder 13 is provided with an absorber 2, and the support frame 1 is further opened with a fitted aperture 18, the film box body 16 is respectively provided with a directional input interface 17 in communication with the liquid bottle 4 and a needle 20 via an infusion pipe and a directional output interface 14 with a gas identifier 15, the film box body 16 is installed with a fast assembling head restraint 41 and an elastic film 27, and a transmission system 31 is arranged at a side of the elastic film 27, where the transmission system 31 includes a miniature direct current motor 32 connected to a frequency modulating system 28, the miniature direct current motor 32 is connected to a spiral straightening device 34 via a speed reducer 33, and the spiral straightening device 34 is connected to a reciprocating film propping device 36 via a two-order shaft 43, a truncated cone 39 of the reciprocating film propping device 36 at a front end is in contact with the elastic film 27, the frequency modulating system 28 includes a miniature direct current power source 30 connected to the miniature direct current motor 32, the miniature direct current power source 30 is further connected to a controller 11 for controlling the miniature direct current motor 32 via a potentiometeric sensor 29, and the controller 11 is further connected with a controller parameter input keyboard 12, the controller 11 is further installed with an acousto-optical warning display 42 and a transmitter 19 in connection with a weight sensor of the liquid bottle; when weight of liquid medicine in the liquid bottle is lower than a preset value, the weight sensor of the liquid medicine inputs a signal to the acousto-optical warning display 42 of the controller 11 for warning and displaying, meanwhile the signal is transmitted to a nurse station to remind medical staff via the transmitter 19. The infusion pipe between the film box body 16 and the needle is further provided with a liquid medicine heating control system 22, the liquid medicine heating control system 22 includes a pagoda-type heater 25 enwinding the infusion pipe in contact with a heating power source 24, the pagoda-type heater 25 is installed with a temperature sensor 26 at an end, the pagoda-type heater 25 and the temperature sensor 26 are connected to a temperature controller 23 respectively, and an infusion pipe at a front end of the needle is provided with a liquid medicine precision filter 21.

The reciprocating film propping device 36 includes a flat body 37, a course adjusting mechanism 40 mounted in a sliding sleeve 45, a trapezoidal transition section 38 and the truncated cone 39 which are arranged from back to front sequentially, and the trapezoidal transition section 38 is mounted with a plate-type spring 44, an outer side of the flat body 37 is further installed with a distance sensor 35 in connection with the controller 11, a rear end of the flat body 37 is further installed with a speed rotatable handle 10 for adjusting flow rate of liquid within the film box body, a speed selecting pointer 8 installed on the speed rotatable handle 10, and an infusion speed dial 9 corresponding to the speed selecting pointer 8.

The present invention consists of the following major components:

1. a transmission system, 2. a film box body, 3. a miniature auxiliary function system includes an infusion speed regulating device, a controller, a remote real-time display, an acousto-optical warning device, a miniature liquid infusion medicine constant temperature control device.

The transmission system converts electrical energy (a miniature chargeable high energy battery) into reciprocating motion for power production by enabling a miniature direct current motor to drive a speed reducer into rotary motion and pass through a spiral straightening wheel, and then transfers the power produced from reciprocating motion to a course adjusting mechanism via a two-order shaft so as to make it be subject to reciprocating motion for power production. Trapezoidal double-headed screw threads are designed within the sliding sleeve, which match with an adjusting rod screw threads within the sliding sleeve to become a complex of the reciprocating motion for power production.

The reciprocating film propping device is a central part to achieve an adjusting function, the component is designed with a truncated cone contact at a front end, of which the forepart is designed with trapezoidal double-headed screw threads, and the tail is designed with a flat body. The flat body is suited with a hard-connected potentiometer part, an end of the flat body is suited with a hard-connected rotatable handle with a pointer, the rotatable handle pointer is corresponding to a dial disc (graduations from 0 to 300°) secured to the casing. The elastic film of the film box body is pushed to generate infusion force via the truncated cone contact on the reciprocating film propping device, and a course distance is adjusted to reach an amplitude target via the trapezoidal double-headed screw threads on the reciprocating film propping device, a potentiometer on the reciprocating film propping device reaches a collection target of amplitude modulating signals, the rotatable handle with the pointer and the dial disc on the adjusting rod form a flow rate input mechanism.

The present invention implements a hard-connected procedural mechanism by a conversion process from electrical energy→mechanical energy→infusion force, a mechanisms transmission process of energies, and a mechanisms adjusting process, functions thereof will be briefly described hereunder: when the rotatable handle pointer points at a 0° position (0°), the truncated cone of the reciprocating film propping device is in contact with the elastic film at a 0° distance. When the rotatable handle pointer is adjusted to point at a 30° position, the trapezoidal double-headed screw threads of the reciprocating film propping device rotate forward, and chord height of arc formed by the truncated cone contact pressing into the elastic film of the film box body is equal to 6×30°/360° mm, meanwhile a miniature potentiometer suited on the flat body of the reciprocating film propping device also rotates by 30°, and transmits a corresponding potential difference signal.

When the rotatable handle pointer is adjusted to a 120° position, the trapezoidal double-headed screw threads of the adjusting rod rotate and then move forward, and chord height of arc formed by the truncated cone contact pressing into the elastic film of the film box body is equal to 6×120°/360° mm, meanwhile the potentiometer suited on the flat body also rotates by 120° synchronously, and transmits a corresponding potential difference signal, and the like.

Regulate infusion speed via amplitude of a trigger: adjust course of the adjusting rod, that is, adjust chord height of arc formed by the contact pressing into the elastic film. The chord height of arc of the elastic film is then $y=ax^2$ which has a relationship with amplitude and infusion quantity.

$$\text{Formula: } Q = \frac{\pi}{3} H(R^2 + R_n^2 + R \cdot R_n) \times 75 \text{ times/min} \times 10^{-3} \text{(ml)}$$

Figure 5:
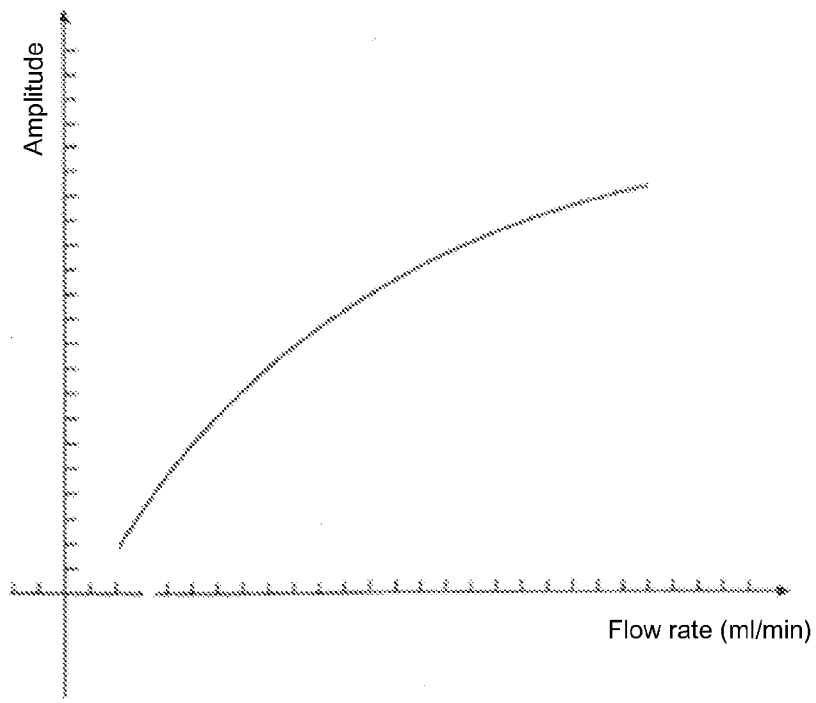
FIG. 5 is a graph of relationship between amplitude and flow rate of a reciprocating film propping device according to the present invention.

R is a radius of an upper circle of the truncated cone, $R_n$ is a radius of a lower circle of the truncated cone, H is a chord height of arc, $R_n$=1.35+0.391 H, units thereof are mm, $Q_n$ is flow rate (ml/min), 75 times/min is a rated frequency, a process of above energy conversion, energy mechanical transmission and amplitude modulation is as shown in the figure (FIG. 5).

Figure 6:
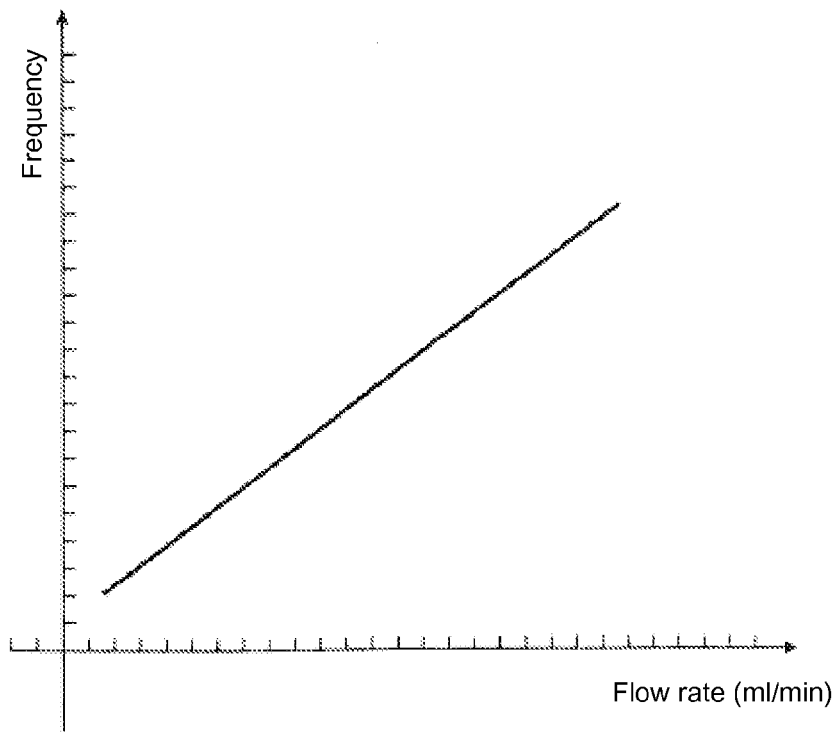
FIG. 6 is a graph of relationship between frequency and flow rate of a reciprocating film propping device according to the present invention.

Regulate infusion speed via frequency of the trigger: see FIG. 6.

A frequency modulating process is implemented by setting a frequency modulation system: frequency modulation is implemented by a potentiometeric sensor which is connected in a power supply circuit of a micro-motor in series, when the micro-motor runs to produce power, power of the motor varies with a varying voltage supplied thereto, and revolution number of the motor changes correspondingly, that is, the rotation speed is adjusted, frequency of reciprocating motion is changed via the spiral straightening device, (75 times/min←→0 times/min), that is to say, time of reciprocating pulse is changed, a change in the impulsive force releasing time is reached, which is reflected in change of injection force during the infusion process, equivalent to an action of slowly pushing the needle during the injection.

In a condition where the motor load (overcoming infusion resistance) is stable, the infusion speed is also stable. Adjusting of motor rotation rate of the potentiometer has a valid adjusting range, this range determines infusion accuracy, for instance, in a range of 25°-325°, then the accuracy is adjusted: accuracy of selected flow rate (5 ml/min) for adjusting 1° is: 5 ml/min×1/300=0.0166 ml, i.e. 0.33%, thereby realizing accurate control of the infusion speed, a change in a relationship between the flow rate and the frequency is $y=ax$: $Q=Q_{H1}\times HZ$, $$Q_{H1} = \frac{Q_H}{\text{rated frequency}\left(\frac{750}{\text{min}}\right)} \times HZ,$$

HZ is a selected frequency (times/min), $Q_{H1}$ is an infusion speed (ml/min), $Q_H$ is an inherent flow rate.

A miniature energy conversion system (a host machine) is guidance of a design scheme: ① a "drip" infusion technique is a microscopic theory which focuses on the drip. Each drip is about 0.15 ml, it is a relative minor power production process that injecting 0.15 ml drip to a height (lift) of about 2 m, energy consumption thereof should be little, and thus it should be available to use a miniature motor at a milliwatt level as the infusion force. Experiments turn to be successful via simulations. Thus, foundations are laid for the design scheme. It is in FIG. 3 where a miniature motor of 350 milliwatts is used. ② for a conversion technique of the spiral straightening wheel, it can be seen from the figure that, conversion of an track-inclined slot of the spiral straightening wheel is a reciprocating linear motion for power production, forces are transferred to the infusion adjusting rod via the two-order shaft to complete drip infusion power production. It is a key component for power conversion, which makes it possible for the entire mechanical transmission mechanism to realize miniaturization, and get succeeded. ③ a high efficiency energy-saving technique: it can be seen from FIG. 3 that, the track-inclined slot of the spiral straightening wheel is inserted with a ball bearing of Φ 1.5×2 mm, and the two-order shaft is installed with a ball bearing of Φ 6×4 mm at a guided hole, they transfer output power of the motor to an amplitude modulating mechanism via two miniature bearings. Degree deviation between the adjusting sleeve and the fixed sliding barrel center is controlled in a range of 10-20 uμ, a gap is controlled in a range of 0.05 mm-0.1 mm, and fine molybdenum disulfide is used for lubrication. The loss of extra work in the conversion and power conversion is reduced to a relatively low level. Upon practical tests, a lithium battery of 4.5 cm×3 cm×2.5 cm may support the operation of the miniature motor for more than 200 hours of infusion.

Technique of a fast-assembling head restraint:

Linkup of a disposable film box infusion device and a host machine requires fast-assembling and secured connections. It can be seen from FIG. 3 that, a three-pin plug of the film box body is inserted into the fast-assembling head restraint, and is rotated by 60°, the plug cap is pressed into a circular semi-blind hole by a plate-type spring to be elastically compressed, the three-pin plug of the film box body is firmly locked therein, which may be disassembled only through two actions, pressing downward and rotating towards the left. Compared with a common fast-assembling mechanism, this device is peerless for its convenience, safe and secured assembling. The power conversion system becomes simple, portable and reliable through application of the innovative techniques above.

Figure 3:
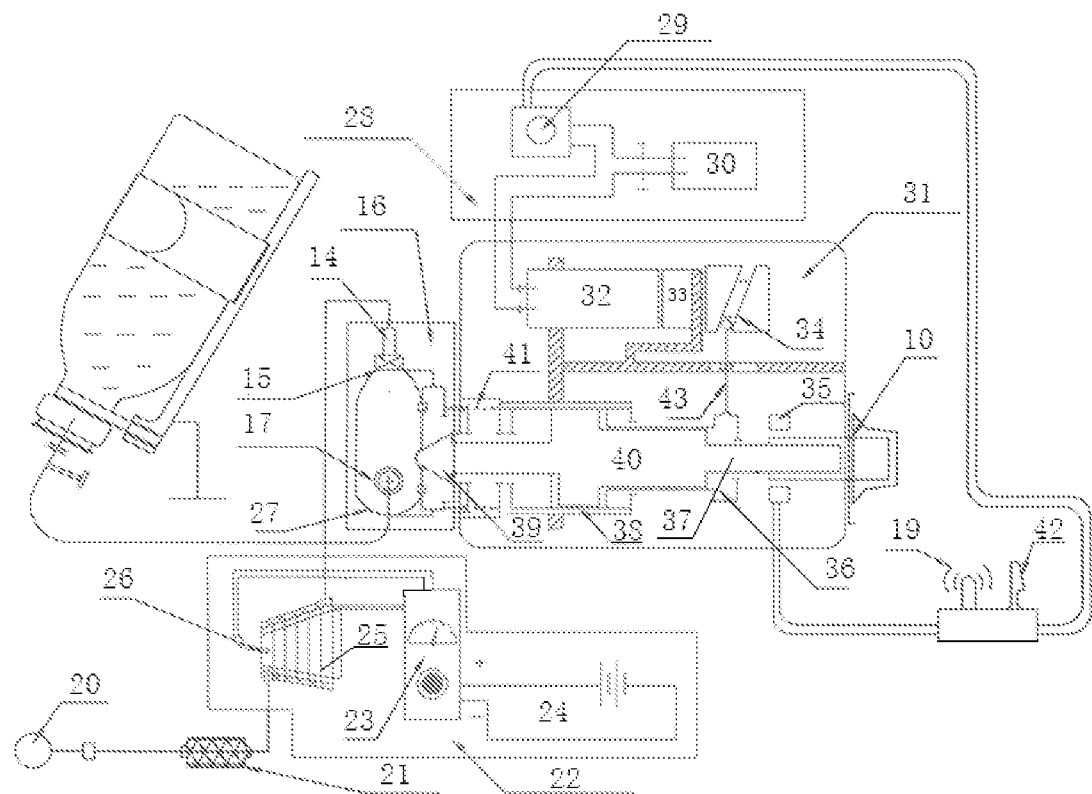
FIG. 3 is a schematic diagram of the overall structure of a miniature portable multifunctional infusion device according to the present invention.
Figure 4:
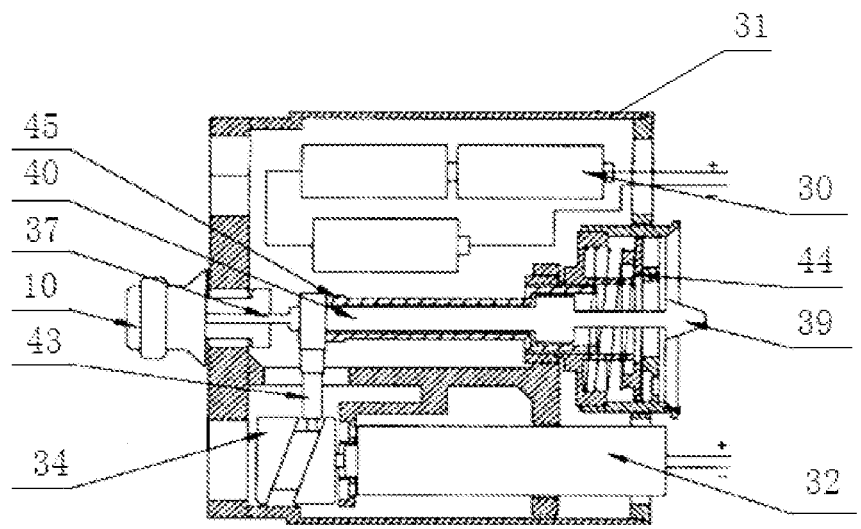
FIG. 4 is a schematic structural diagram of a transmission system according to the present invention.

Infusion temperature self-controlled system:

In order to improve comfort of the infusion, solve cold stimulation and adverse reaction from the injected liquid medicine to a patient in a cold environment without heating installations, a set of infusion temperature self-controlled system is placed in the portable infusion device, as shown in FIG. 3: the system is composed of a miniature liquid medicine heater, a miniature temperature controller and a heating power source. The liquid medicine heater is a pagoda-type heater with spiral grooves which is processed by duralumin, resembling like a snail, an end of the infusion pipe is partially entwined in the grooves by 0.4-0.6 m, a soft resistor disc which is connected to the direct current power source is provided at the bottom of the grooves, and a miniature temperature sensor is inserted at the end section of the infusion pipe which comes out of the grooves. Heating temperature of the miniature temperature controller is controlled in a range of 15° C.-25° C. The heater is in operation when the temperature is below 15° C., and the heater undergoes an automatic break to stop heating when the temperature reaches 25° C. This system is an independent system, which does not incur interference and functional impacts to the portable multifunctional infusion device.

What is claimed is:

1. A miniature portable multifunctional infusion device, comprising: a support frame (1), a liquid bottle (4) and a film box body (16) secured thereto, wherein the film box body (16) is respectively provided with a directional input interface (17) and a directional output interface (14) in communication with the liquid bottle (4) and a needle (20) via an infusion pipe, the film box body (16) is installed with an elastic film (27), and a transmission system (31) is arranged at a side of the elastic film (27), the transmission system (31) comprises a miniature direct current motor (32) connected to a frequency modulating system (28), the miniature direct current motor (32) is connected to a spiral straightening device (34) via a speed reducer (33), and the spiral straightening device (34) is connected to a reciprocating film propping device (36) via a two-order shaft (43), a truncated cone (39) of the reciprocating film propping device (36) at a front end is in contact with the elastic film (27), the frequency modulating system (28) comprises a miniature direct current power source (30) connected to the miniature direct current motor (32), the miniature direct current power source (30) is further connected to a controller (11) for controlling the miniature direct current motor (32) via a potentiometric sensor (29), and the controller (11) is further connected with a controller parameters input keyboard (12).

2. The miniature portable multifunctional infusion device according to claim 1, wherein: the reciprocating film propping device (36) comprises a flat body (37), a course adjusting mechanism (40) mounted in a sliding sleeve (45), a trapezoidal transition section (38) and the truncated cone (39) which are arranged from back to front sequentially, and the trapezoidal transition section (38) is mounted with a plate-type spring (44).

3. The miniature portable multifunctional infusion device according to claim 2, wherein: an outer side of the flat body (37) is further installed with a distance sensor (35) in connection with the controller (11).

4. The miniature portable multifunctional infusion device according to claim 2, wherein: a rear end of the flat body (37) is further installed with a speed rotatable handle (10) for adjusting flow rate of liquid within the film box body, a speed selecting pointer (8) installed on the speed rotatable handle (10), and an infusion speed dial (9) corresponding to the speed selecting pointer.

5. The miniature portable multifunctional infusion device according to claim 1, wherein: the film box body (16) is further installed with a flow rate display (7).

6. The miniature portable multifunctional infusion device according to claim 1, wherein: the infusion pipe between the film box body (16) and the needle is further provided with a liquid medicine heating control system (22), the liquid medicine heating control system (22) comprises a pagoda-type heater (25) enwinding the infusion pipe in contact with a heating power source (24), the pagoda-type heater (25) is installed with a temperature sensor (26) at an end, the pagoda-type heater (25) and the temperature sensor (26) are connected to a temperature controller (23) respectively, and an infusion pipe at a front end of the needle is provided with a liquid medicine precision filter (21).

7. The miniature portable multifunctional infusion device according to claim 1, wherein: the support frame (1) comprises a bottle holder (46) installed with the liquid bottle (4) and a crescent holder (13) installed with the film box body (16), the bottle holder (46) is provided with a binder (3), a head restraint (5) and an adjusting foundation (6) which fasten the liquid bottle (4), the crescent holder (13) is provided with an absorber (2), and the support frame (1) is further opened with a fitted aperture (18).

8. The miniature portable multifunctional infusion device according to claim 1, wherein: the film box body (16) is further provided with a fast-assembling head restraint (41).

9. The miniature portable multifunctional infusion device according to claim 1, wherein: the directional output interface (14) is further provided with a gas identifier (15).

10. The miniature portable multifunctional infusion device according to claim 1, wherein: the controller (11) is installed with an acousto-optical warning display (42) and a transmitter (19) in connection with a weight sensor of the liquid bottle.

* * * * *